United States Patent
Amiot et al.

(10) Patent No.: US 11,672,613 B2
(45) Date of Patent: Jun. 13, 2023

(54) ROBOTIZED SYSTEM FOR FEMOROACETABULAR IMPINGEMENT RESURFACING

(71) Applicant: MedTech S.A., Montpellier (FR)

(72) Inventors: Louis-Philippe Amiot, Montreal (CA); Seth Anderson Nash, Fort Wayne, IN (US); John R. White, Winona Lake, IN (US)

(73) Assignee: MedTech S.A., Montpellier (FR)

( * ) Notice: Subject to any disclaimer, the term of this patent is extended or adjusted under 35 U.S.C. 154(b) by 0 days.

(21) Appl. No.: 17/668,138

(22) Filed: Feb. 9, 2022

(65) Prior Publication Data

US 2022/0265366 A1 Aug. 25, 2022

Related U.S. Application Data

(62) Division of application No. 16/786,522, filed on Feb. 10, 2020, now abandoned, which is a division of
(Continued)

(51) Int. Cl.
*G06T 7/00* (2017.01)
*A61B 34/20* (2016.01)
(Continued)

(52) U.S. Cl.
CPC ........ *A61B 34/20* (2016.02); *A61B 17/00234* (2013.01); *A61B 17/1764* (2013.01);
(Continued)

(58) Field of Classification Search
None
See application file for complete search history.

(56) References Cited

U.S. PATENT DOCUMENTS

| 8,548,559 B2 | 10/2013 | Hodgson et al. |
| 8,764,760 B2 | 7/2014 | Metzger et al. |

(Continued)

FOREIGN PATENT DOCUMENTS

| CN | 109310477 A | 2/2019 |
| WO | WO-2013020026 A1 | 2/2013 |

(Continued)

OTHER PUBLICATIONS

"U.S. Appl. No. 15/625,555, Examiner Interview Summary dated Sep. 19, 2019", 3 pgs.
(Continued)

*Primary Examiner* — Edward Park
(74) *Attorney, Agent, or Firm* — Schwegman Lundberg & Woessner, P.A.

(57) ABSTRACT

Systems and methods are described herein for resurfacing bones, and in particular, for detecting and resurfacing one or more femoroacetabular impingements (FAIs). A FAI resurfacing controller may be used to perform this detecting and resurfacing of FAIs. The FAI resurfacing controller may include a bone model generator to receive bone imaging and to generate a model of at least one osteophyte and of a surface of a native bone surrounding the at least one osteophyte. The FAI resurfacing controller may include an osteophyte identifier to set a virtual 3D boundary surface between native bone surface and the at least one osteophyte. The FAI resurfacing controller may include a resurfacing navigator to generate and output a navigation file. The navigation file may include the model with the 3D boundary surface between native bone surface and the at least one osteophyte.

20 Claims, 6 Drawing Sheets

Related U.S. Application Data application No. 15/625,555, filed on Jun. 16, 2017, now Pat. No. 10,582,971.

(60) Provisional application No. 62/350,891, filed on Jun. 16, 2016.

(51) Int. Cl.

| | | |
|---|---|---|
| *A61B 34/10* | (2016.01) | |
| *A61B 34/30* | (2016.01) | |
| *A61B 17/00* | (2006.01) | |
| *A61B 17/17* | (2006.01) | |
| *A61B 90/00* | (2016.01) | |

(52) U.S. Cl.
CPC .............. *A61B 34/10* (2016.02); *A61B 34/30* (2016.02); *A61B 17/175* (2013.01); *A61B 17/1746* (2013.01); *A61B 2034/105* (2016.02); *A61B 2034/2046* (2016.02); *A61B 2034/2057* (2016.02); *A61B 2034/2065* (2016.02); *A61B 2090/3983* (2016.02)

(56) References Cited

U.S. PATENT DOCUMENTS

| | | | |
|---|---|---|---|
| 8,888,782 | B2 | 11/2014 | Smith et al. |
| 9,113,971 | B2 | 8/2015 | Metzger et al. |
| 9,386,993 | B2 | 7/2016 | Meridew et al. |
| 9,629,642 | B2 | 4/2017 | Johannaber |
| 9,717,510 | B2 | 8/2017 | Smith et al. |
| 10,582,971 | B2 | 3/2020 | Amiot et al. |
| 2007/0156157 | A1 | 7/2007 | Nahum et al. |
| 2007/0249967 | A1 | 10/2007 | Buly et al. |
| 2009/0112214 | A1* | 4/2009 | Philippon ............ A61B 17/025 606/191 |
| 2010/0292731 | A1* | 11/2010 | Gittings ............ A61B 17/0401 606/232 |
| 2011/0015639 | A1 | 1/2011 | Metzger et al. |
| 2012/0041446 | A1 | 2/2012 | Wong et al. |
| 2013/0083984 | A1 | 4/2013 | Chabanas et al. |
| 2013/0211531 | A1 | 8/2013 | Steines et al. |
| 2013/0338490 | A1 | 12/2013 | Wendler |
| 2014/0188240 | A1 | 7/2014 | Lang et al. |
| 2014/0228860 | A1 | 8/2014 | Steines et al. |
| 2015/0351778 | A1 | 12/2015 | Uthgenannt et al. |
| 2016/0278793 | A1 | 9/2016 | Meridew et al. |
| 2017/0112508 | A1 | 4/2017 | Paradis et al. |
| 2017/0360513 | A1 | 12/2017 | Amiot et al. |
| 2020/0170721 | A1 | 6/2020 | Amiot et al. |

FOREIGN PATENT DOCUMENTS

| | | |
|---|---|---|
| WO | WO-2014145691 A1 | 9/2014 |
| WO | WO-2014198796 A1 | 12/2014 |
| WO | WO-2017218933 A1 | 12/2017 |

OTHER PUBLICATIONS

"U.S. Appl. No. 15/625,555, Examiner Interview Summary dated Sep. 26, 2019", 3 pgs.

"U.S. Appl. No. 15/625,555, Final Office Action dated Jul. 22, 2019", 16 pgs.

"U.S. Appl. No. 15/625,555, Non Final Office Action dated Jan. 18, 2019", 16 pgs.

"U.S. Appl. No. 15/625,555, Notice of Allowance dated Nov. 1, 2019", 8 pgs.

"U.S. Appl. No. 15/625,555, Response filed Apr. 18, 2019 to Non Final Office Action dated Jan. 18, 2019", 13 pgs.

"U.S. Appl. No. 15/625,555, Response filed Oct. 22, 2019 to Final Office Action dated Jul. 22, 2019", 14 pgs.

"U.S. Appl. No. 16/786,522, Final Office Action dated Nov. 9, 2021", 7 pgs.

"U.S. Appl. No. 16/786,522, Non Final Office Action dated Jun. 16, 2021", 10 pgs.

"U.S. Appl. No. 16/786,522, Response filed Aug. 2, 2021 to Non Final Office Action dated Jun. 16, 2021", 10 pgs.

"Canadian Application Serial No. 3,027,964, Office Action dated Dec. 12, 2019", 4 pgs.

"Canadian Application Serial No. 3,027,964, Response filed Apr. 14, 2020 to Office Action dated Dec. 12, 2019", 19 pgs.

"Chinese Application Serial No. 201780036192.3, Office Action dated Apr. 14, 2021", w/ English Translation, 12 pgs.

"Chinese Application Serial No. 201780036192.3, Office Action dated Sep. 2, 2020", w/ English translation, 14 pgs.

"Chinese Application Serial No. 201780036192.3, Response filed Mar. 17, 2021 to Office Action dated Sep. 2, 2020", w/ English claims, 11 pgs.

"Chinese Application Serial No. 201780036192.3, Response filed Jun. 11, 2021 to Office Action dated Apr. 14, 2021", w/ English claims, 10 pgs.

"Chinese Application Serial No. 201780036192.3, Response filed Aug. 13, 2021", with English claims, 5 pages.

"Clinical Graphics", Job 122044, (Aug. 11, 2015), 5 pgs.

"European Application Serial No. 17734206.0, Response filed Aug. 5, 2019 to Office Action dated Jan. 25, 2019", 24 pgs.

"International Application Serial No. PCT/US2017/037940, International Preliminary Report on Patentability dated Dec. 27, 2018", 10 pgs.

"International Application Serial No. PCT/US2017/037940, International Search Report dated Sep. 7, 2017", 7 pgs.

"International Application Serial No. PCT/US2017/037940, Written Opinion dated Sep. 7, 2017", 10 pgs.

Dandachli, W., et al., "Analysis of cover of the femoral head in normal and dysplastic hips. New CT-based technique.", J Bone Joint Surg Br 90-B, (2008), 1428-1434.

Kohnlein, Werner, et al., "Acetabular Morphology, Implications for Joint-preserving Surgery", Clinical orthopaedics and related research; 467 (3), (2009), 682-691.

Tannast, Moritz, et al., "Hip Pain in the Young Adult", EFORT European Instructional Lectures., (2011), 141-154.

Toogood, Paul A., et al., "Proximal Femoral Anatomy in the Normal Human Population", Clinical orthopaedics and related research; 467 (4), (2009), 876-885.

"Canadian Application Serial No. 3,113,815, Examiner's Rule 86(2) Requisition Report, dated Aug. 2, 2022, 4 pgs.", 4 pgs.

"Canadian Application Serial No. 3,113,815, Response filed Nov. 29, 2022 to Examiner's Rule 86(2) Requisition Report dated Aug. 2, 2022, 18 pgs.", 18 pgs.

* cited by examiner

ROBOTIZED SYSTEM FOR FEMOROACETABULAR IMPINGEMENT RESURFACING

CLAIM OF PRIORITY

This application is a divisional of U.S. patent application Ser. No. 16/786,522, filed Feb. 10, 2020, which is a divisional of U.S. patent application Ser. No. 15/625,555, filed on Jun. 16, 2017, now issued as U.S. Pat. No. 10,582,971, which claims the benefit of U.S. Provisional Patent Application Ser. No. 62/350,891, filed on Jun. 16, 2016, the benefit of priority of each of which is claimed hereby, and each of which is incorporated by reference herein in its entirety.

FIELD

The present application relates to computer-assisted orthopedic surgery involving robotized apparatuses.

BACKGROUND

Computer-assisted surgery has been developed to help an operator in altering bones, and in positioning and orienting implants to a desired orientation. Among the various tracking technologies used in computer-assisted surgery, optical navigation, C-arm validation, and manual reference guides have been used. The optical navigation typically requires the use of a navigation system, which adds operative time. Moreover, the optical navigation is bound to line-of-sight constraints that hamper the normal surgical flow. C-arm validation requires the use of bulky equipment, and the C-arm validation is not cost-effective.

Such tracking technologies often assist manual work performed by an operator or surgeon. While surgeons may have developed an expertise in manipulations performed during surgery, some practitioners prefer the precision and accuracy of robotized surgery.

DETAILED DESCRIPTION

The present disclosure describes a robotic system for resurfacing bones, and in particular, for detecting and resurfacing one or more femoroacetabular impingements (FAIs). A FAI resurfacing controller may be used to perform this detecting and resurfacing of FAIs. The FAI resurfacing controller may include a bone model generator to receive bone imaging and to generate a model of at least one osteophyte and of a surface of a native bone surrounding the at least one osteophyte. The FAI resurfacing controller may include an osteophyte identifier to set a virtual 3D boundary surface between native bone surface and the at least one osteophyte. The FAI resurfacing controller may include a resurfacing navigator to generate and output a navigation file. The navigation file may include the model with the 3D boundary surface between native bone surface and the at least one osteophyte. The navigation file may also include patient-specific numerical control data for resurfacing the bone to remove the at least one osteophyte.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

Figure 1:
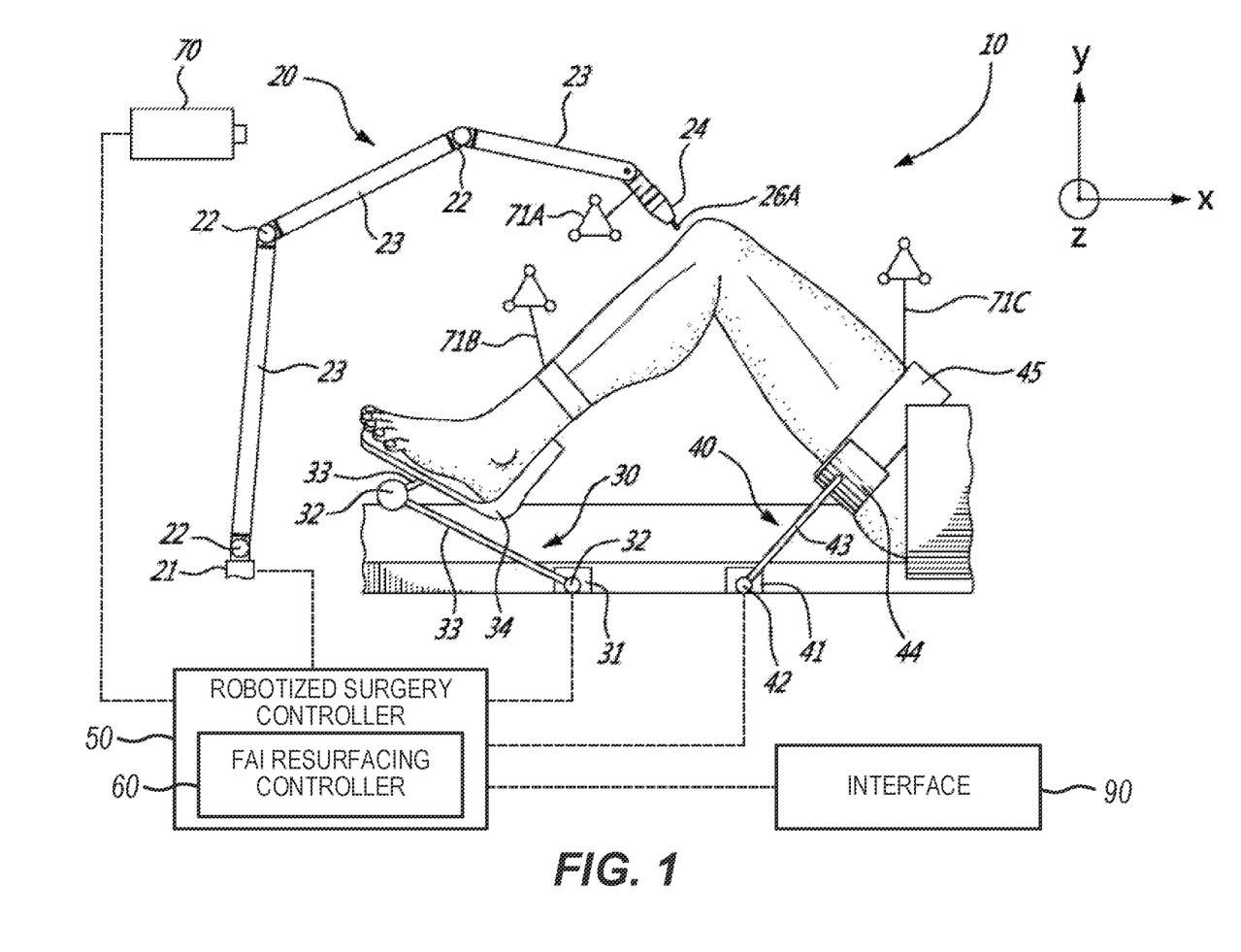
FIG. 1 is a schematic view of a robotized surgery system, in accordance with some embodiments.

FIG. 1 is a schematic view of a robotized surgery system 10, in accordance with some embodiments. Robotized surgery system 10 may be used to perform orthopedic surgery maneuvers on a patient, such as FAI resurfacing, arthroscopy, or other surgical procedures. The robotized surgery system 10 is shown relative to a patient's leg in a supine decubitus, though the patient may be in lateral decubitus (e.g., to expose the hip joint) or in another position.

The robotized surgery system 10 may include a robot arm 20, a foot support 30, a thigh support 40, a robotized surgery controller 50, a FAI resurfacing controller 60, and a supplementary tracking apparatus 70. The robot arm 20 is the working end of the system 10, and is used to perform bone alterations as planned by an operator and as controlled by the robotized surgery controller 50. The robot arm 20 is positioned to access the hip joint of the patient for performing FAI resurfacing. The foot support 30 supports the foot and lower leg of the patient, in such a way that it is only selectively movable for adjustment to the patient's position and morphology. The thigh support 40 supports the thigh and upper leg of the patient, again in such a way that it is only optionally movable. The thigh support 40 may assist in keeping the hip joint fixed during FAI resurfacing, and should hence be positioned so as not to impede the movements of the robot arm 20. The robotized surgery controller 50 controls the robot arm 20. The FAI resurfacing controller 60 output data used to drive the robot arm 20 in performing the FAI resurfacing. The tracking apparatus 70 may optionally be used to track the robot arm 20 and the patient limbs.

The robot arm 20 may stand from a base 21, for instance in a fixed relation relative to the operating room (OR) table supporting the patient. Indeed, the relative positioning of the robot arm 20 relative to the patient is a determinative factor in the precision of the surgical procedure, whereby the foot support 30 and thigh support 40 may assist in keeping the operated limb fixed in the illustrated {X Y Z} coordinate system. The robot arm 20 has a plurality of joints 22 and links 23, of any appropriate form, to support a tool head 24 that interfaces with the patient. The arm 20 is shown being a serial mechanism, arranged for the tool head 24 to be displaceable in sufficient degrees of freedom (DOF). For example, the robot arm 20 controls 6-DOF movements to the tool head 24, {X Y Z} in the coordinate system, and pitch, roll, and yaw. Fewer or additional DOFs may be present. For simplicity, only a generic illustration of the joints 22 and links 23 is provided, but more joints of different types may be present to move the tool head 24 in the manner described above. The joints 22 are powered for the robot arm 20 to move as controlled by the controller 50 in the six DOFs. Therefore, the powering of the joints 22 is such that the tool head 24 of the robot arm 20 may execute precise movements, such as moving along a single direction in one translation DOF, or being restricted to moving along a plane, among possibilities. Various types of robot arms 20 may be used, such as those described in U.S. patent application Ser. No. 11/610,728, incorporated herein by reference.

The tool head 24 may also comprise a chuck or like tool interface, typically actuatable in rotation. In FIG. 1, the tool head 24 supports a burr 26A, such as may be used during FAI resurfacing. The tool head 24 may support other surgical tools, such as a registration pointer, a reamer, a cannula, a reciprocating saw, or another surgical tool. The various tools may be interchanged, whether with human assistance, or as an automated process. The installation of a tool in the tool head 24 may then require some calibration to position the installed tool in the {X Y Z} coordinate system of the robot arm 20. Various surgical procedures may be performed when tool head 24 is used with a cannula. In an example, the robot arm 20 may be used to perform a robotically assisted arthroscopy procedure. A shaver, burr, suture applicator, or another surgical instrument may be operated through the cannula. The controller 50 may target the cannula using sensors within the robot arm 20, such as sensors used to detect position or rotation of various components of the robot arm 20. The controller 50 may target the cannula using one or more cameras mounted on the tracking apparatus 70.

Tracking apparatus 70 may include various types of tracking systems depending on the particular surgical application. For example, the tracking apparatus 70 may be used to track the robot arm 20 or other components of the surgery system 10 using one or more image capture devices (e.g., cameras). The tracking apparatus 70 may include an arthroscopic camera for viewing the surgical site in a minimally invasive manner. The tracking apparatus 70 may also be used to provide video recognition and tracking-guided surgery procedures. For example, the controller 50 may use the tracking apparatus 70 to detect an unhealthy acetabular labrum, place the cannula in a predetermined location, and stitch the acetabular labrum. The tracking apparatus 70 can also include an associated controller or computing system to processing data received from various sensors (e.g., cameras, etc.) to provide guidance to other components of the system. For example, in an optical tracking scenario, the tracking apparatus 70 can include at least two cameras coupled to a computing system that utilizes images captured from the cameras to triangulate positions of tracked objects. In another example, the tracking apparatus 70 can include an arthroscopic camera and a computing device that receives image data and performs image processing operations to segment information out of the image data related to osteophyte removal.

The tracking apparatus 70 may also be used to verify removal of one or more osteophytes. A primary source of error during surgical procedures involving removal of osteophytes is the failure to completely remove the osteophyte, which may be due to the difficulty in determining how much of an osteophyte has been removed. The controller 50 may use the tracking apparatus 70 and robot arm 20 to determine how much of the osteophyte has been removed and whether the osteophyte removal process is complete. In an example, a feedback mechanism may be used to indicate when the osteophyte has been removed. The feedback may include a green light, an audible feedback, a tactile feedback, or other feedback. The determination of whether the osteophyte has been removed may be based on an image from the tracking apparatus 70, based on comparing the burr 26A location against a 3D model, based on manual leg manipulation and tracking range of movement through the tracking apparatus 70, or based on another osteophyte removal confirmation.

The controller 50 may drive the robot arm 20 in performing the surgical procedure based on the planning achieved pre-operatively. The robotized surgery controller 50 runs various modules, in the form of algorithms, code, non-transient executable instructions, etc., to operate the system 10 in the manner described herein. For example, the controller 50 may include a robot driver module, where the robot driver module is tasked with powering or controlling the various joints of the robot arm 20. Force feedback may be provided by the robot arm 20 to avoid damaging the soft tissue or surrounding environment. The robotized surgery controller 50 may have a processor unit to control movement of the robot arm 20. System 10 may include an interface 90 to provide information to the operator. The interface 90 may include a display, a wireless portable electronic device (e.g., phone, tablet), a speaker for audio guidance, an LED display, or other type of interface.

The controller 50 may be used to drive the robot arm 20 to avoid various predetermined soft tissues. In an embodiment, the controller 50 may use the tracking apparatus 70 to detect a particular soft tissue and drive the robot arm 20 to avoid that soft tissue. In an embodiment, the controller 50 may identify a safety zone, and may guide the robot arm 20 to enforce a safety zone by avoiding performing surgical procedures within the safety zone during a surgical procedure. In various examples, the safety zone may include surrounding soft tissue, a native bone surface of a patient, or a critical blood vessel (e.g., femoral artery, neck artery).

Figure 2:
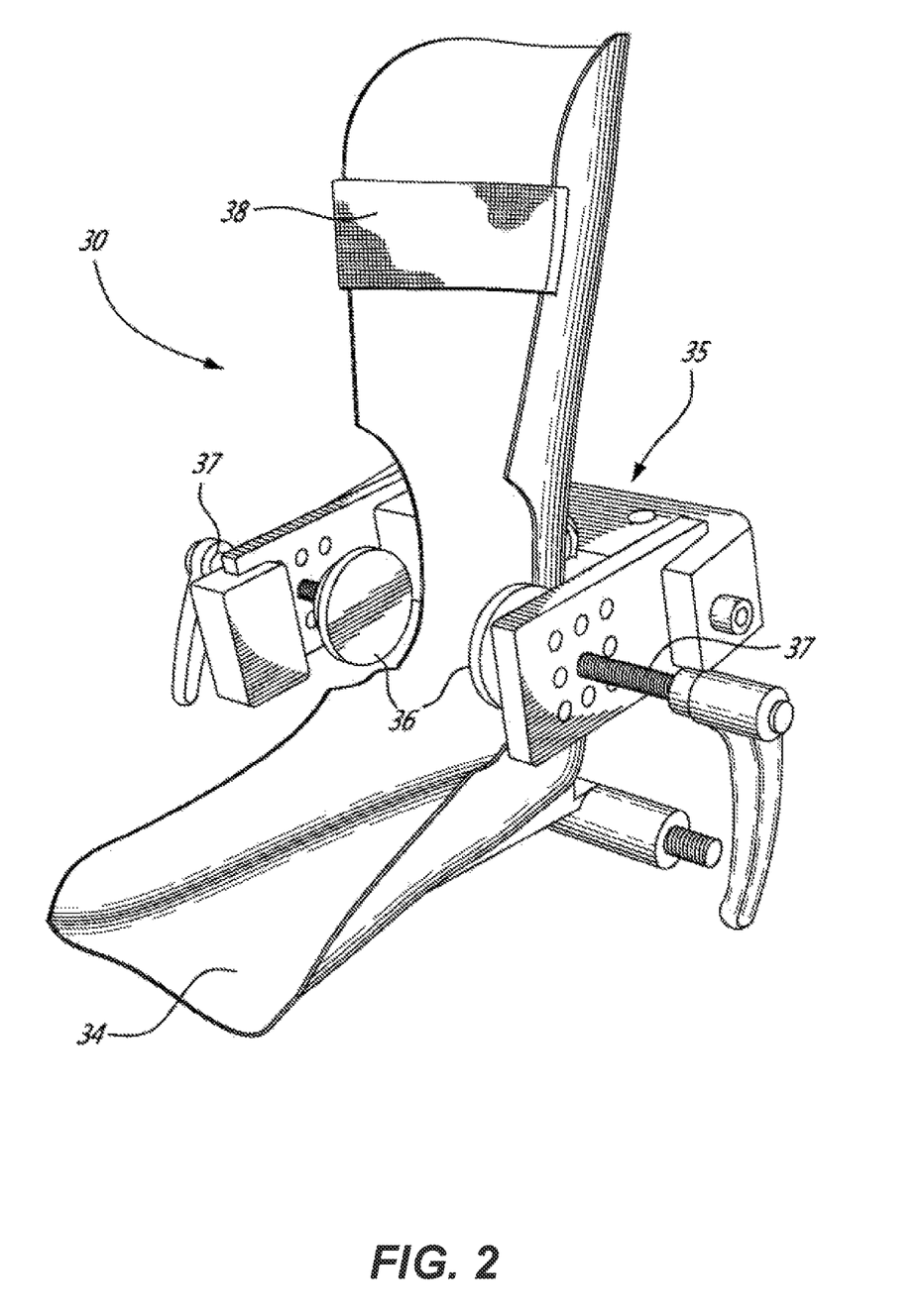
FIG. 2 is an exemplary perspective view of a foot support of the robotized surgery system of FIG. 1, in accordance with some embodiments.

To preserve the fixed relation between the leg and the coordinate system, a generic embodiment of a foot support 30 is shown in FIG. 1, while one possible implementation of the foot support 30 is shown in greater detail in FIG. 2. The foot support 30 may be displaceable relative to the OR table, to adjust to the patient, with the joints then lockable once a suitable position is reached. The mechanism of the foot support 30 may have a slider 31, moving along the OR table in the X-axis direction. Joints 32 and links 33 may also be part of the mechanism of the foot support 30, to support a foot interface 34 receiving the patient's foot.

The thigh support 40 may be displaceable relative to the OR table, to be better positioned as a function of the patient's location on the table, so as not to impede action of the robot arm 20. Accordingly, the thigh support 40 is shown as including a passive mechanism, with various lockable joints to lock the thigh support 40 in a desired position and orientation. The mechanism of the thigh support 40 may have a slider 41, moving along the OR table in the X-axis direction. Joints 42 and links 43 may also be part of the mechanism of the thigh support 40, to support a thigh bracket 44. A strap 45 can immobilize the thigh/femur in the thigh support 40. The thigh support 40 may not be necessary in some instances.

The foot support 30 or the thigh support 40 may assist in keeping the bones fixed relative to the {X Y Z} coordinate system. For instance, the fixed relation may be required in instances in which no additional tracking is present to assist the actions of the robot arm 20. However, the tracking apparatus 70 may provide intraoperative tracking information for the robot arm 20 and for the patient bones, in such a way that some movement of the patient is permissible intraoperatively as the movement is calculable and thus known in the {X Y Z} coordinate system.

The operation of the tracking apparatus 70 may depend on the information within the navigation file C. For example, the tracking apparatus 70 may assist in performing the calibration of the patient bone with respect to the robot arm 20, for subsequent navigation in the {X Y Z} coordinate system. The tracking apparatus 70 may include two cameras to provide stereoscopic (e.g., 3D) image data to optically identify and locate retro-reflective references 71A, 71B, and 71B to triangulate positions of objects associated with the references. In an embodiment, the reference 71A is on the tool head 24 of the robot arm 20 such that its tracking allows the controller 50 to calculate the position and/or orientation of the tool head 24 and tool 26A thereon. In an example, reference 71A may be etched on a stable portion of a burr tool 26A. The controller 50 may use information about the position of the tool head 24 and the camera on the tracking apparatus 70 to adjust the camera to optimize the collected images, such as adjusting camera position, camera angle, camera distance from tool head 24, focal length, or other dynamic camera adjustments. The tracking apparatus 70 may also include a robot tracking arm, and the controller 50 may control the robot tracking arm to adjust the camera position or perform other dynamic camera adjustments. The robot tracking arm may be controlled independently or in conjunction with controlling the robot arm 20.

In addition to reference 71A on the tool head 24, references 71B and 71C may be fixed to the patient bones, such as the tibia for reference 71B and the femur for reference 71C. In an example, references 71B and 71C are applied to the patent bones using a brief procedure to provide rapid reference tracking. In another example, references 71B and 71C may include application of a virtual marker (e.g., "painted on") to an image of the bone, such as using interface 90. In FAI resurfacing, it may only be necessary to have the reference 71C, although it may be desired to have another reference on the pelvis as well, depending on the location of the osteophytes. As shown, the references 71 attached to the patient need not be invasively anchored to the bone, as straps or like attachment means may provide sufficient grasping to prevent movement between the references 71 and the bones, in spite of being attached to soft tissue. For example, the references 71 may include a fabric removably and non-invasively attachable to a bone, where references 71 each include a plurality of reference markers distributed on the surface of the fabric. The controller 50 continuously updates the position or orientation of the robot arm 20 and patient bones in the {X Y Z} coordinate system using the data from the tracking apparatus 70. Tracking system 70 may include one or more of optical tracking sensors, inertial tracking sensors, or other motion or location sensors. For example, tracking system 70 may include inertial sensors (e.g., accelerometers, gyroscopes, etc.) that produce tracking data to be used by the controller 50 to update the position or orientation of the robot arm 20 continuously. Other types of tracking technology may also be used.

The calibration may be achieved in the manner described above, with the robot arm 20 using a registration pointer on the robot arm 20, and with the assistance of the tracking apparatus 70 if present in the robotized surgery system 10. Another calibration approach is to perform radiography of the bones with the references 71 thereon, at the start of the surgical procedure. For example, a C-arm may be used for providing suitable radiographic images. The images are then used for the surface matching with the bone model B of the patient. Because of the presence of the references 71 as fixed to the bones, the intraoperative registration may then not be necessary, as the tracking apparatus 70 tracks the position or orientation of the bones in the {X Y Z} coordinate system after the surface matching between X-ray and bone model is completed.

FIG. 2 is an exemplary perspective view of a robotized surgery system foot support 30, in accordance with some embodiments. The foot interface 34 may have an L-shaped body ergonomically shaped to receive the patient's foot. To fix the foot in the foot support 33, different mechanisms may be used, one of which features an ankle clamp 35. The ankle clamp 35 surrounds the rear of the foot interface 34, and laterally supports a pair of malleolus pads 36. The malleolus pads 36 are positioned to be opposite the respective malleoli of the patient, and are displaceable via joints 37, to be brought together and hence clamp onto the malleoli. A strap 38 may also be present to secure the leg in the foot support 30 further, for example by attaching to the patient's shin. As an alternative to the arrangement of FIG. 2, a cast-like boot may be used, or a plurality of straps 38, provided the foot is fixed in the foot support 33.

Figure 3A:
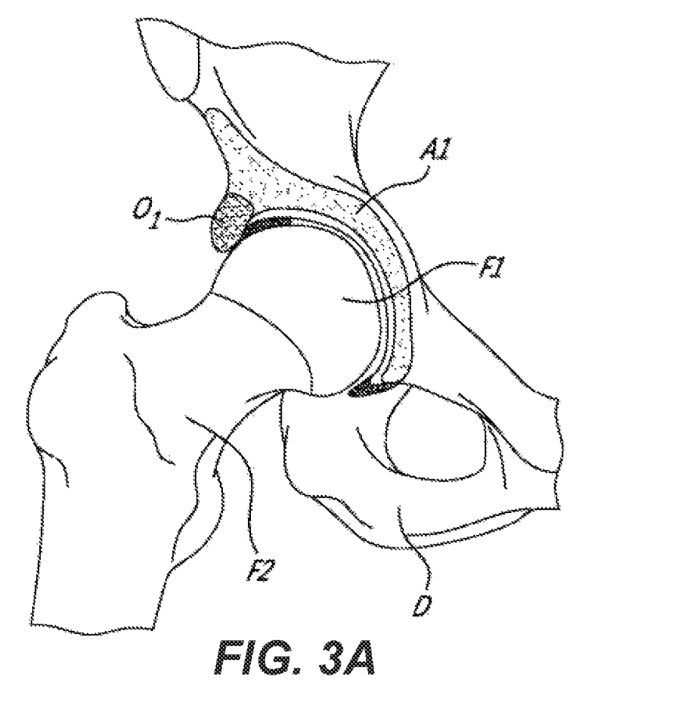
FIG. 3A is a perspective schematic view of femoroacetabular impingement (FAI) conditions on the pelvis, in accordance with some embodiments.
Figure 3B:
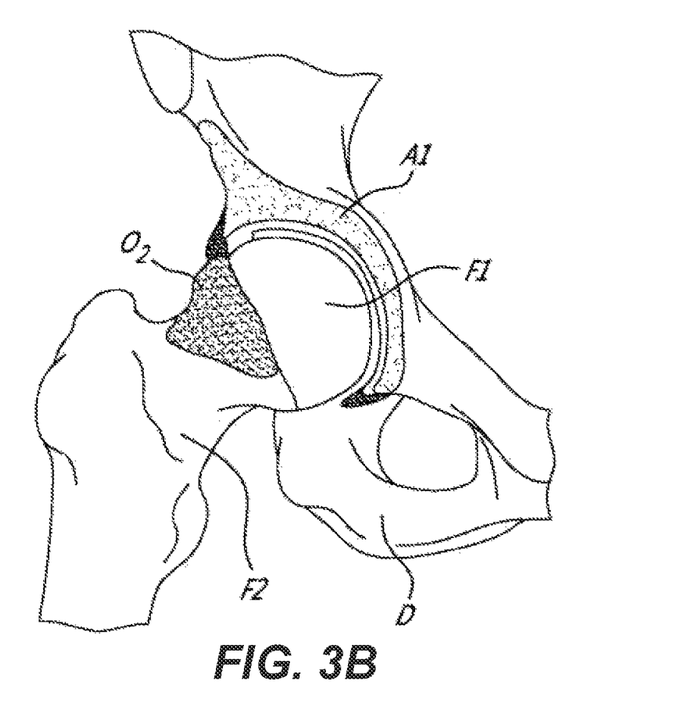
FIG. 3B is a perspective schematic view of FAI conditions on the femoral head and neck, in accordance with some embodiments.

FIG. 3A is a perspective schematic view of FAI conditions on the pelvis D, in accordance with some embodiments. FIG. 3B is a perspective schematic view of FAI conditions on the femoral head F1 and neck F2, in accordance with some embodiments. The system 10 is used to resurface the femoral head F1 or neck F2, or to resurface the periphery of the acetabulum A1 in a FAI condition. The FAI condition may be caused by one or more osteophytes on the rim of the acetabulum A1 or femoral head F1 or neck F2. In FIG. 3A, osteophyte O1 is shown built up on the periphery of the acetabulum A1, part of the pelvis D. This acetabular bone growth may be known as a pincer deformity, and may cause a pincer impingement. In FIG. 3B, osteophyte O2 is shown built up at the junction of the femoral head F1 and femoral neck F2, part of the pelvis D. This femoral bone growth may be known as a cam deformity, and may cause a femoral cam impingement. One or both of the pincer deformity and cam deformity may occur, and both may be corrected using the FAI resurfacing techniques described herein. FIGS. 3A and 3B are examples of possible osteophyte locations, but other osteophytes can build up at other locations.

Figure 4:
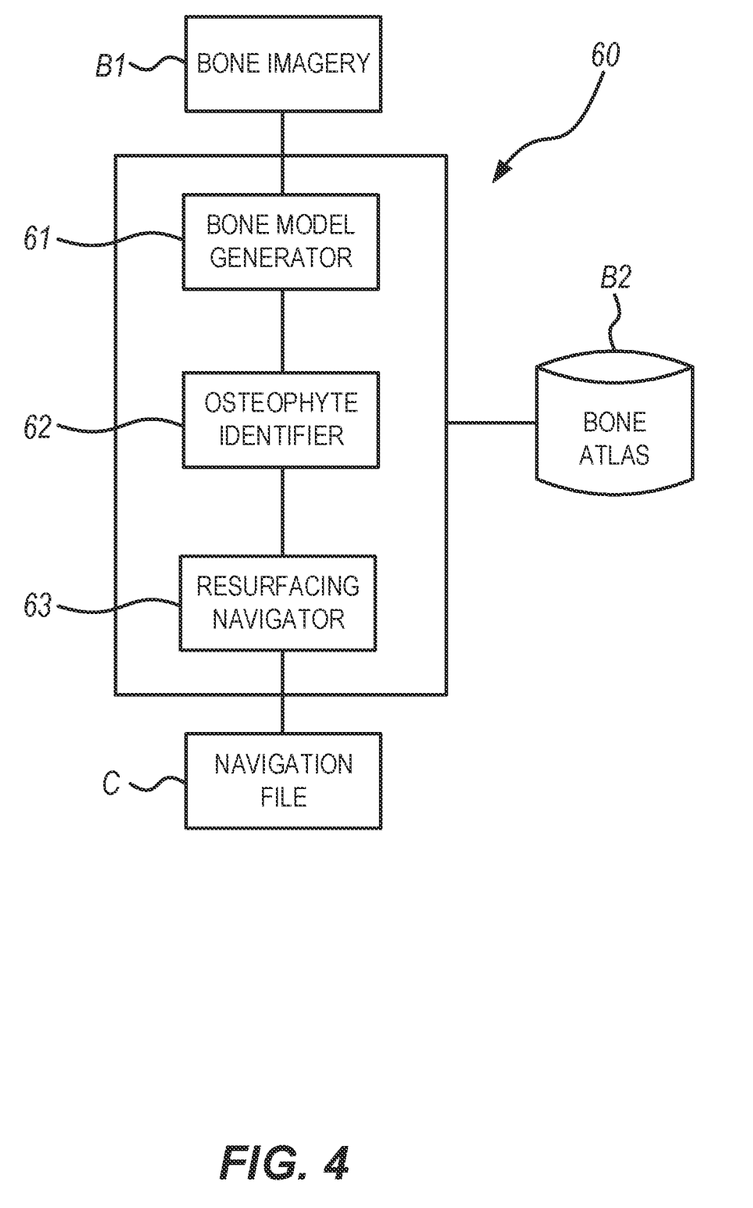
FIG. 4 is a block diagram of a FAI resurfacing controller used with the robotized surgery system of FIG. 1, in accordance with some embodiments.

FIG. 4 is a block diagram of a FAI resurfacing controller used with the robotized surgery system of FIG. 1, in accordance with some embodiments. To drive the robot arm 20 in resurfacing the hip joint, in either or both conditions of FIGS. 3A and 3B, a navigation file C may be created. Referring to FIG. 4, a FAI resurfacing controller is generally shown at 60. The controller 60 may be part of the system 10, for example as part of a set of modules that are in the robotized surgery controller 50. The FAI resurfacing controller 60 may also be a stand-alone processing unit, used in pre-operative planning to prepare a navigation file C.

The FAI resurfacing controller 60 may receive bone imagery B1. The bone imagery B1 may include a computed tomography (CT) scan image, magnetic resonance imaging (MRI) image, or any other radiography imagery. A bone model generator module 61 receives the bone imagery B1 to generate a bone model therefrom. The model may be a 3D representation of at least a portion of the surface having osteophytes thereon. For example, the 3D representation may be that of a portion of the acetabulum A1 or of a portion of the femoral head F1 and neck F2. The 3D representation may include a portion of the bone surface surrounding the osteophytes, and the osteophytes.

An osteophyte identifier module 62 receives the bone model, and segments the osteophyte from the native bone surface. Various approaches may be used for the segmentation by the osteophyte identifier module 62. According to an embodiment, the osteophyte identifier module 62 consults a bone atlas database B2. The bone atlas database B2 includes a compilation of different femur or pelvis geometries, for instance also as 3D bone models. The osteophyte identifier module 62 compares the bone model, particularly the native bone surface surrounding the osteophyte, with bone geometries of the database B2 to find closest matches. Once a closest match is identified, the bone models may be overlaid to define a surface of the patient bone covered by osteophytes.

Various geometric features may be used by the osteophyte identifier module 62 to identify an osteophyte. In an example, the received bone model may be used to identify geometric features of the bone, and the osteophytes may be identified by identifying differences between bone model geometric features and a bone atlas databases match. In another example, one or more femoral or acetabular geometric measurements may be used to identify geometric features of the bone. The geometric measurements may include an alpha angle, a lateral center edge angle, a femoral head coverage, a sourcil angle, an acetabular angle, or other femoral or acetabular geometric measurements. In an example, the alpha angle may be used to characterize the concavity of the anterior femoral head-neck junction, or how big the bump is on the femoral neck. The alpha angle is defined as the acute angle between the femoral neck axis and a line between the femoral head center with the point where the head-neck junction cortical surface first meets with a circle superimposed upon an ideally spherical femoral head. The alpha angle may be particularly useful in detecting an osteophyte that causes or contributes to a femoral cam impingement. In another example, the lateral center edge angle may be used to characterize the angular coverage of the femoral head by the weight-bearing zone of the acetabulum. The lateral center edge angle is defined as the angle formed by intersection of a vertical line extending through the femoral head center and a line extending through the femoral head center to the lateral sourcil. The lateral center edge angle may be particularly useful in detecting an osteophyte that contributes to acetabular dysplasia, acetabular instability, or femoral impingement. In another example, the femoral head coverage may be used to characterize weight-bearing femoral head coverage, where the femoral head coverage is defined as the percentage coverage of the femoral head by the weight-bearing zone of the acetabulum. The femoral head coverage may be particularly useful in detecting an osteophyte that contributes to acetabular dysplasia or pincer impingement, and may also be used when resurfacing the acetabular rim due to pincer impingement. In another example, the sourcil angle may be used to characterize the angle-dependent coverage of the femoral head by the acetabulum. The sourcil angle (e.g., Tonnis angle) is defined as the angle formed between a horizontal line and a line extending from the medial edge of the sourcil to the lateral edge of the sourcil. The sourcil angle may be particularly useful in detecting an osteophyte that contributes to acetabular dysplasia, acetabular instability, or femoral impingement. In another example, the acetabular angle may be used to characterize the acetabular inclination or opening. The acetabular angle may include the acetabular angle of Sharp, defined as the angle formed between a horizontal line and a line from the teardrop to lateral acetabulum. The acetabular angle may include the acetabular roof angle of Tonnis, defined as the angle formed by a horizontal line connecting both triradiate cartilages (e.g., the Hilgenreiner line) and a second line connecting the acetabular roofs. The acetabular angle may be particularly useful in detecting an osteophyte that contributes to pincer impingement. Once the osteophyte identifier module 62 analyzes the bone geometry to identify the osteophyte, the geometric features may be used by the resurfacing navigator 63 to achieve a desired geometric goal or to correspond with a preoperatively planned geometric goal. For example, the osteophyte identifier module 62 may identify the alpha angle, which may be used by the resurfacing navigator 63 to achieve a desired alpha angle or to correspond with a preoperatively planned alpha angle.

In an embodiment, the osteophyte identifier module 62 may analyze the bone model directly, such as by generating a 3D model based on the bone model and determining an impingement-free range of motion. For example, the osteophyte identifier module 62 may perform 3D reconstruction along the neck of the femur, identify the center of the sphere of the femoral head, and identify the non-spherical portions to determine impingement-free range of motion. Accordingly, the osteophyte identifier module 62 virtually segments the native bone surface from the osteophyte, by defining a 3D boundary surface between the native bone and the osteophyte.

In the model generated by the osteophyte identifier module 62, the 3D boundary surface is affixed and surrounded by the 3D bone model of the bone model generator module 61. The osteophyte identifier module 62 may alternatively or supplementally require the assistance of an operator. For instance, the 3D boundary surface based on the bone atlas data B2 may be a starting point for an operator to perform adjustments to the virtual segments or other virtual boundaries. As another example, the osteophyte identifier module 62 may provide the bone model to the bone model generator module 61, along with interactive virtual tools, for an operator to define a 3D boundary surface between the osteophyte and the native bone surface. The interactive virtual tool may include a suggested 3D boundary surface based on extensions of the native bone surrounding the osteophytes.

A resurfacing navigator 63 uses the bone model with 3D boundary surface to generate the navigation file C. The navigation file C may include the bone model with 3D boundary surface, with a high enough surface resolution of native bone surface surrounding the 3D boundary surface for an intraoperative registration to be executed by the robot arm 20, in a calibration. The calibration may include the bone model B of the patient, for surface matching to be performed by a registration pointer of the robot arm 20. The robot arm 20 would obtain a cloud of bone landmarks of the exposed bones, to reproduce a 3D surface of the bone. The 3D surface would then be matched to the bone model B of the patient, to set the 3D model in the {X Y Z} coordinate system. If a bone model is not available, a bone model may be generated intraoperatively. For example, a surgical registration pointer may be used to contact a bone surface to register a point, and multiple points may be synthesized to generate a cloud of small surfaces representing an approximate bone model.

The resurfacing navigator 63 may also include a resurfacing path for the robot arm 10 based on a model of the osteophyte, and an identification of the tool that may be used, such as the burr 26A shown in FIG. 1. The resurfacing path may consider the surrounding soft tissue to be minimally invasive, such as by defining a safety zone to avoid specific soft tissues. The resultant navigation file C defines the maneuvers to be performed by the robot arm 20 as directed by the controller 50 of the system 10. The resultant navigation file C may include a patient-specific numerical control data, such as anatomical information specific to the patient to aid in navigating the robot arm 20. The maneuvers may be performed by the robot arm 20 without surgeon intervention.

Figure 5:
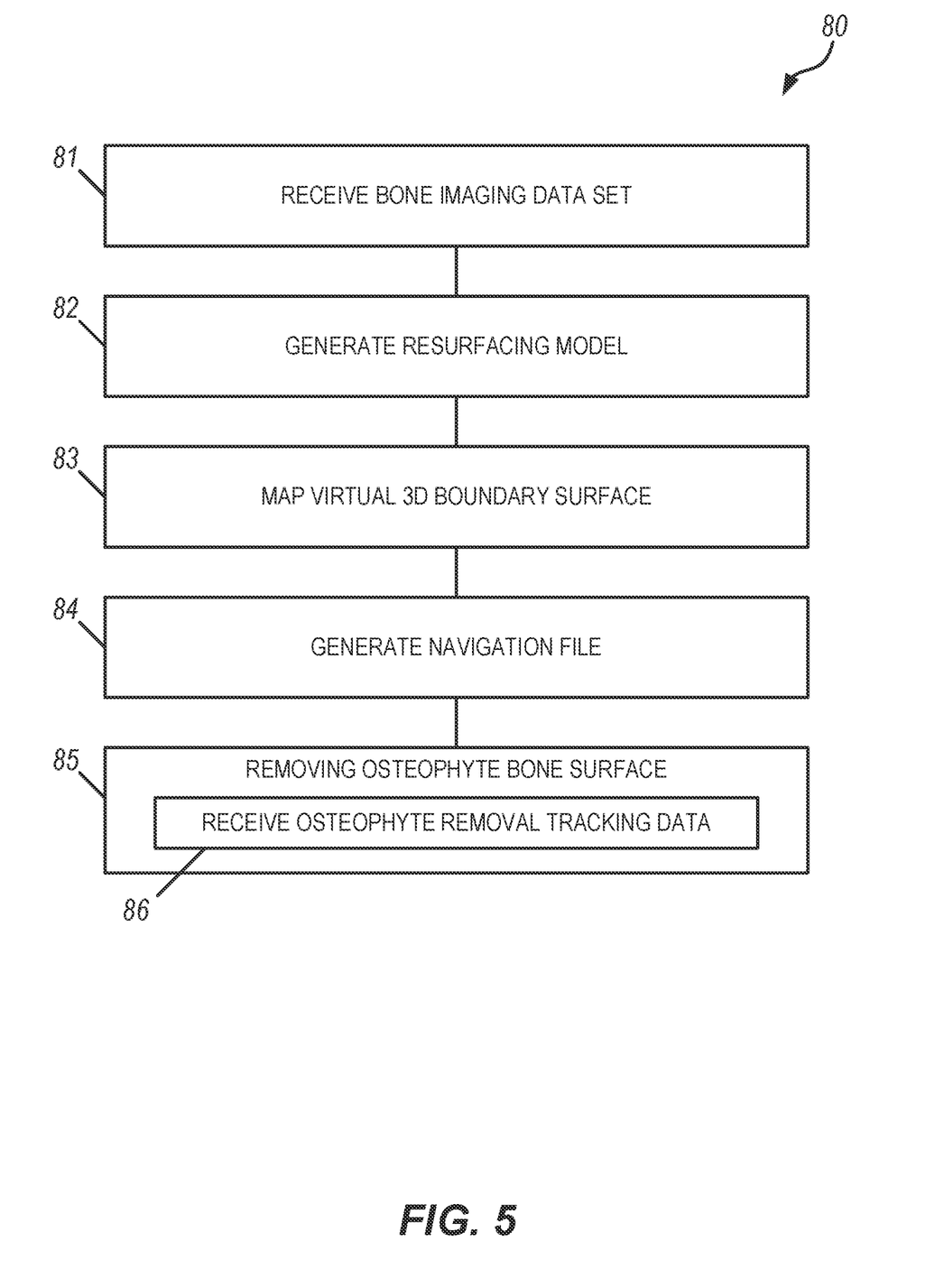
FIG. 5 illustrates a flow chart showing a robotized surgery system technique for FAI resurfacing, in accordance with some embodiments.

FIG. 5 illustrates a flow chart showing a robotized surgery system technique 80 for FAI resurfacing, in accordance with some embodiments. In an embodiment, technique 80 is performed autonomously by a robotized system for femoroacetabular impingement resurfacing. The robotized system may include one or more of the components of the robotized surgery system 10 described above, such as robotized surgery controller 50, robotic arm 20, tracking system 70, or other component. In particular, the robotized surgery controller 50 may include an FAI resurfacing controller 60, which may include a bone model generator 61, an osteophyte identifier 62, and a resurfacing navigator 63. Technique 80 may include receiving 81 a bone imaging data set at a bone model generator 61. The bone imaging data set may include an x-ray image, a computed tomography (CT) scan image, MRI imaging, or any other radiography imagery that can provide sufficient detail to allow identification of osteophytes. The bone model generator 61 may generate 82 a resurfacing model. The resurfacing model may include at least one osteophyte and a native bone surface surrounding the at least one osteophyte. As discussed above, generating 82 the resurfacing model can optionally include manual intervention through a graphical user interface provided to a surgeon or technician. The osteophyte identifier 62 may map 83 a virtual 3D boundary surface based on the resurfacing model. The virtual 3D boundary surface may identify an osteophyte virtual boundary located between the native bone surface and the at least one osteophyte. The resurfacing navigator 63 may generate 84 a navigation file. The navigation file may include the resurfacing model, the virtual 3D boundary surface, and a plurality of patient-specific numerical control data. The navigation file can include control vectors used by the surgery controller 50 to direct a cutting tool attached to the robotic arm 20 to remove the identified osteophytes. The surgery controller 50 may execute the navigation file to direct the robotic arm in automatically removing 85 the at least one osteophyte from the native bone surface based on the navigation file. Removing 85 the at least one osteophyte may include the surgery controller 50 receiving 86 tracking data from a tracking system 70. The surgery controller 50 may further direct the cutting tool attached to the robotic arm 20 based on tracking data received from the tracking system 70. Regardless of whether a tracking device is used, the robotic arm may remove 85 the at least one osteophyte without surgeon intervention. In an embodiment, the surgery controller 50 may generate or update a 3D model based on tracking data received 86 from the tracking system 70 to verify osteophyte removal. For example, the surgery controller 50 may update the 3D model to confirm the current state of the resurfaced bone provides impingement-free range of motion. In addition to the surgery controller 50 verifying osteophyte removal, a surgeon may manipulate a joint intraoperatively and provide osteophyte removal confirmation or other feedback to the surgery controller 50.

Figure 6:
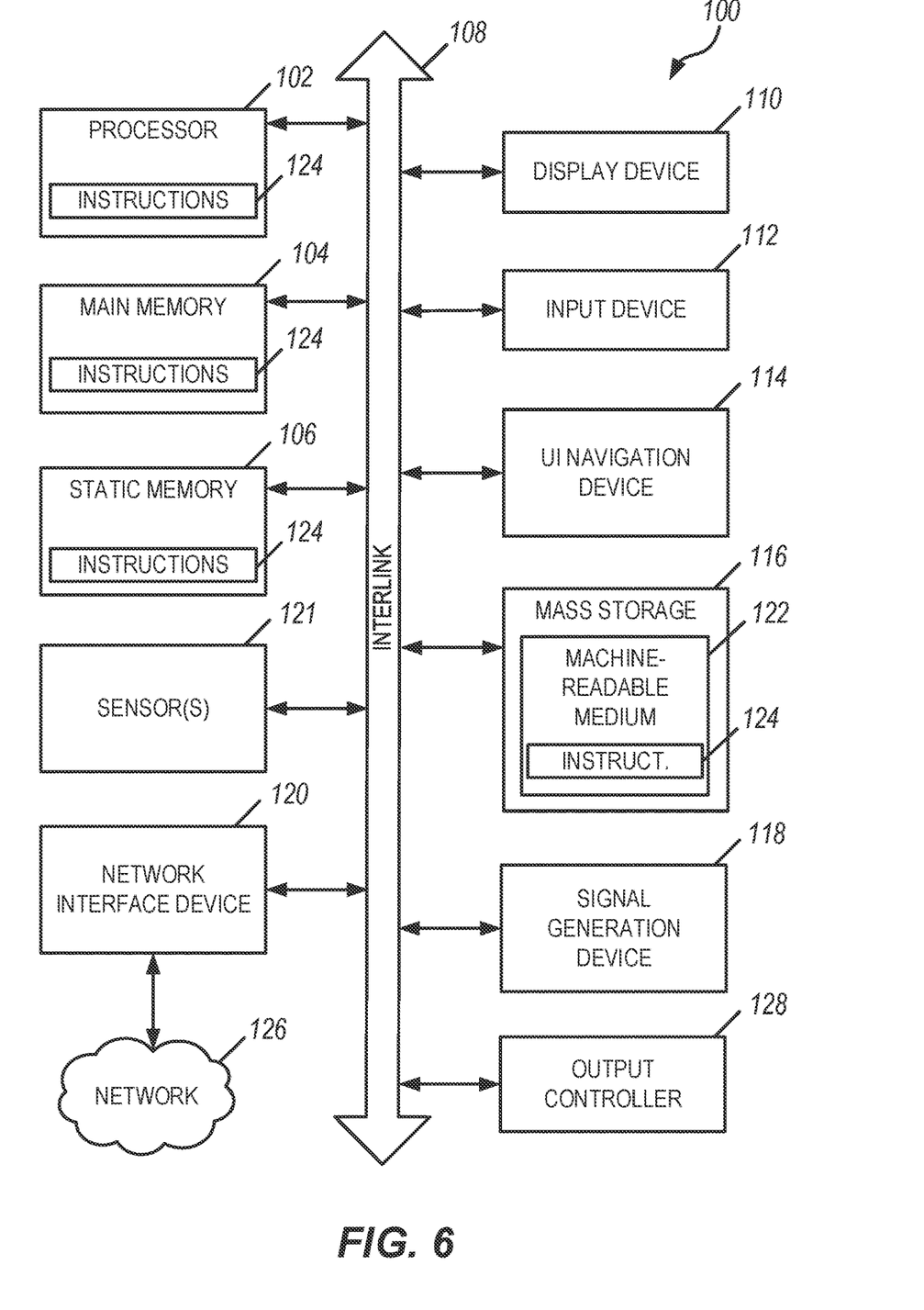
FIG. 6 illustrates generally an example of a block diagram of a machine upon which any one or more of the techniques (e.g., methodologies) discussed herein may perform in accordance with some embodiments.

FIG. 6 illustrates generally an example of a block diagram of a machine 100 upon which any one or more of the techniques (e.g., methodologies) discussed herein may perform in accordance with some embodiments. In alternative embodiments, the machine 100 may operate as a standalone device or may be connected (e.g., networked) to other machines. In a networked deployment, the machine 100 may operate in the capacity of a server machine, a client machine, or both in server-client network environments. The machine 100 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 100 may include a hardware processor 102 (e.g., a central processing unit (CPU), a graphics processing unit (GPU), a hardware processor core, or any combination thereof), a main memory 104 and a static memory 106, some or all of which may communicate with each other via an interlink (e.g., bus) 108. The machine 100 may further include a display unit 110, an alphanumeric input device 112 (e.g., a keyboard), and a user interface (UI) navigation device 114 (e.g., a mouse). In an example, the display unit 110, alphanumeric input device 112 and UI navigation device 114 may be a touch screen display. The display unit 110 may include goggles, glasses, an augmented reality (AR) display, a virtual reality (VR) display, or another display component. For example, the display unit may be worn on a head of a user and may provide a heads-up-display to the user. The alphanumeric input device 112 may include a virtual keyboard (e.g., a keyboard displayed virtually in a VR or AR setting.

The machine 100 may additionally include a storage device (e.g., drive unit) 116, a signal generation device 118 (e.g., a speaker), a network interface device 120, and one or more sensors 121, such as a global positioning system (GPS) sensor, compass, accelerometer, or other sensor. The machine 100 may include an output controller 128, such as a serial (e.g., universal serial bus (USB), parallel, or other wired or wireless (e.g., infrared (IR), near field communication (NFC), etc.) connection to communicate or control one or more peripheral devices.

The storage device 116 may include a machine readable medium 122 that is non-transitory on which is stored one or more sets of data structures or instructions 124 (e.g., software) embodying or utilized by any one or more of the techniques or functions described herein. The instructions 124 may also reside, completely or at least partially, within the main memory 104, within static memory 106, or within the hardware processor 102 during execution thereof by the machine 100. In an example, one or any combination of the hardware processor 102, the main memory 104, the static memory 106, or the storage device 116 may constitute machine readable media.

While the machine readable medium 122 is illustrated as a single medium, the term "machine readable medium" may include a single medium or multiple media (e.g., a centralized or distributed database, or associated caches and servers) configured to store the one or more instructions 124.

The term "machine readable medium" may include any medium that is capable of storing, encoding, or carrying instructions for execution by the machine 100 and that cause the machine 100 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 124 may further be transmitted or received over a communications network 126 using a transmission medium via the network interface device 120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 120 may include one or more physical jacks (e.g., Ethernet, coaxial, or phone jacks) or one or more antennas to connect to the communications network 126. In an example, the network interface device 120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 100, and includes digital or analog communications signals or other intangible medium to facilitate communication of such software.

Various Notes & Examples

Each of these non-limiting examples may stand on its own, or may be combined in various permutations or combinations with one or more of the other examples.

Example 1 is a femoroacetabular impingement resurfacing system comprising: a bone model generator to receive a bone imaging data set and generate a resurfacing model based on the bone imaging data set, the resurfacing model including at least one osteophyte and a native bone surface connected to the at least one osteophyte; an osteophyte identifier to map a virtual 3D boundary surface based on the resurfacing model, the virtual 3D boundary surface identifying an osteophyte virtual boundary located between the native bone surface and the at least one osteophyte; a resurfacing navigator to generate a navigation file, the navigation file including the resurfacing model and the virtual 3D boundary surface, the navigation file to provide control instructions to resurface the native bone surface to remove the at least one osteophyte; and an osteophyte removal device to automatically resurface the native bone surface based on the navigation file.

In Example 2, the subject matter of Example 1 optionally includes wherein the osteophyte removal device includes an osteophyte removal tool, a robotic arm, and a robotic controller; and wherein the robotic controller executes the navigation file to cause the robotic arm to maneuver the osteophyte removal tool to automatically resurface the native bone surface to remove the at least one osteophyte.

In Example 3, the subject matter of Example 2 optionally includes wherein the navigation file includes a safety zone, the safety zone representing a plurality of virtual boundaries that prevent movement of the osteophyte removal device into a plurality of surrounding soft tissues, and wherein the robotic controller uses the navigation file to cause the osteophyte removal device to avoid the safety zone when resurfacing the native bone surface.

In Example 4, the subject matter of any one or more of Examples 1-3 optionally include a tracking apparatus to generate tracking data, wherein the robotic controller processes the tracking data to determine a location of at least one of the osteophyte removal device and the native bone surface.

In Example 5, the subject matter of Example 4 optionally includes wherein the tracking apparatus includes an image capture device to generate image data; and wherein the robotic controller processes the image data to identify and determine the location of at least one of the osteophyte removal device and the native bone surface.

In Example 6, the subject matter of any one or more of Examples 4-5 optionally include wherein the tracking apparatus includes a robotic tracking arm to position the image capture device; and wherein the robotic controller executes the navigation file to control the robotic tracking arm to improve an image quality of the generated image data.

In Example 7, the subject matter of any one or more of Examples 1-6 optionally include a bone atlas database, wherein the osteophyte identifier is further operable to: compare the bone imaging data set against the bone atlas database to find a closest bone atlas entry; and use the closest bone atlas as a model for the native bone surface and to identify the at least one osteophyte.

In Example 8, the subject matter of Example 7 optionally includes wherein the osteophyte identifier identifying the at least one osteophyte includes identifying geometric features based on the bone imaging data set.

In Example 9, the subject matter of any one or more of Examples 1-8 optionally include wherein the osteophyte identifier is further to: generate a 3D bone model based on the bone imaging data set; and determine an impingement-free range of motion based on the 3D bone model.

In Example 10, the subject matter of Example 9 optionally includes D bone model includes: performing a 3D reconstruction along a femoral neck; and identifying a femoral head spherical center.

In Example 11, the subject matter of Example 10 optionally includes D bone model Example 12 is a femoroacetabular impingement resurfacing method comprising: performing the following operations on a computing device including a processor and memory, the operations including: receiving a bone imaging data set; generating a resurfacing model based on the bone imaging data set, the resurfacing model including at least one osteophyte and a native bone surface connected to the at least one osteophyte; mapping a virtual 3D boundary surface based on the resurfacing model, the virtual 3D boundary surface identifying an osteophyte virtual boundary located between the native bone surface and the at least one osteophyte; generating a navigation file, the navigation file including the resurfacing model and the virtual 3D boundary surface, the navigation file to provide control instructions to resurface the native bone surface to remove the at least one osteophyte; and outputting the navigation file for use by an osteophyte removal device to automatically resurface the native bone surface based on the navigation file.

In Example 13, the subject matter of Example 12 optionally includes wherein the osteophyte removal device includes an osteophyte removal tool, a robotic arm, and a robotic controller; and the method further comprises executing the navigation file on the robotic controller to cause the robotic arm to maneuver the osteophyte removal tool to automatically resurface the native bone surface to remove the at least one osteophyte.

In Example 14, the subject matter of Example 13 optionally includes the operations further including generating a safety zone, the safety zone representing a plurality of virtual boundaries that prevent movement of the osteophyte removal device into a plurality of surrounding soft tissues; wherein the navigation file includes instructions to cause the osteophyte removal device to avoid the safety zone when resurfacing the native bone surface.

In Example 15, the subject matter of any one or more of Examples 12-14 optionally include the operations further including determining a location of at least one of the osteophyte removal device and the native bone surface using a tracking system.

In Example 16, the subject matter of Example 15 optionally includes wherein receiving tracking data includes receiving image data from an image capture device; and wherein the operations include processing the image data to identify and determine the location of at least one of the osteophyte removal device and the native bone surface.

In Example 17, the subject matter of Example 16 optionally includes wherein the tracking system includes a robotic tracking arm to position the image capture device; and the method further comprises executing the navigation file to control the robotic tracking arm to improve an image quality of the received image data.

In Example 18, the subject matter of any one or more of Examples 12-17 optionally include the operations further including: comparing the bone imaging data set against a bone atlas database to find a closest bone atlas entry; and use the closest bone atlas as a model for the native bone surface and to identify the at least one osteophyte.

In Example 19, the subject matter of Example 18 optionally includes wherein identifying the at least one osteophyte includes identifying geometric features based on the bone imaging data set.

In Example 20, the subject matter of any one or more of Examples 12-19 optionally include D boundary surface further includes: generating a 3D bone model based on the bone imaging data set; and determining an impingement-free range of motion based on the 3D bone model.

In Example 21, the subject matter of Example 20 optionally includes D bone model includes: performing a 3D reconstruction along a femoral neck; and identifying a femoral head spherical center.

In Example 22, the subject matter of Example 21 optionally includes D bone model.

Example 23 is at least one machine-readable storage medium, comprising a plurality of instructions that, responsive to being executed with processor circuitry of a computer-controlled femoroacetabular impingement resurfacing device, cause the device to: receive a bone imaging data set; generate a resurfacing model based on the bone imaging data set, the resurfacing model including at least one osteophyte and a native bone surface connected to the at least one osteophyte; map a virtual 3D boundary surface based on the resurfacing model, the virtual 3D boundary surface identifying an osteophyte virtual boundary located between the native bone surface and the at least one osteophyte; generate a navigation file, the navigation file including the resurfacing model and the virtual 3D boundary surface, the navigation file to provide control instructions to resurface the native bone surface to remove the at least one osteophyte; and output the navigation file for use by an osteophyte removal device to automatically resurface the native bone surface based on the navigation file.

In Example 24, the subject matter of Example 23 optionally includes wherein the osteophyte removal device includes an osteophyte removal tool, a robotic arm, and a robotic controller; and the instructions further causing the device to execute the navigation file on the robotic controller to cause the robotic arm to maneuver the osteophyte removal tool to automatically resurface the native bone surface to remove the at least one osteophyte.

In Example 25, the subject matter of Example 24 optionally includes the instructions further causing the device to generate a safety zone, the safety zone representing a plurality of virtual boundaries that prevent movement of the osteophyte removal device into a plurality of surrounding soft tissues, wherein the navigation file includes instructions to cause the osteophyte removal device to avoid the safety zone when resurfacing the native bone surface.

In Example 26, the subject matter of any one or more of Examples 23-25 optionally include the instructions further causing the device to determine a location of at least one of the osteophyte removal device and the native bone surface using a tracking system.

In Example 27, the subject matter of Example 26 optionally includes wherein determining the location using a tracking system includes receiving image data from an image capture device within the tracking system; and wherein the determining the location includes processing the image data to identify and determine the location of at least one of the osteophyte removal device and the native bone surface.

In Example 28, the subject matter of Example 27 optionally includes wherein the tracking system includes a robotic tracking arm to position the image capture device; and the method further comprises executing the navigation file to control the robotic tracking arm to improve an image quality of the received image data.

Example 134 is at least one non-transitory machine-readable medium including instructions for operation of a robotic arm, which when executed by at least one processor, cause the at least one processor to perform operations of any of the methods of Examples 1-28.

Example 135 is a method for performing any one of examples 1-28.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. An acetabular labrum repair method comprising:
performing the following operations on a robotized surgery controller device including a processor and memory, the operations including:
receiving acetabular tracking data from an acetabular tracking apparatus;
detecting an unhealthy acetabular labrum based on the acetabular tracking data; and
controlling a robotized acetabular labrum repair device to repair the unhealthy acetabular labrum.

2. The method of claim 1, further including controlling a robotized cannula placement device to place a cannula in a predetermined location to facilitate the repair of the unhealthy acetabular labrum.

3. The method of claim 2, wherein:
the robotized cannula placement device includes a robotized repair device arm to position the robotized acetabular labrum repair device; and
the operations further include controlling the robotized device arm to facilitate the repair of the unhealthy acetabular labrum.

4. The method of claim 1, wherein the acetabular tracking apparatus includes an arthroscopic camera to generate the acetabular tracking data.

5. The method of claim 4, wherein:
the acetabular tracking apparatus is attached to a robotized tracking device arm to position the acetabular tracking apparatus; and
the operations further include controlling the robotized tracking device arm to improve an image quality of the acetabular tracking data.

6. The method of claim 1, the operations further including:
receiving surgery apparatus tracking data from a robotized surgery tracking apparatus; and
determining a location of the robotized acetabular labrum repair device based on the surgery apparatus tracking data.

7. The method of claim 6, wherein:
the surgery apparatus tracking data includes apparatus image data; and
the operations further include processing the apparatus image data to identify and determine the location of the robotized acetabular labrum repair device.

8. The method of claim 1, the operations further including generating a safety zone, the safety zone representing a plurality of virtual boundaries that prevent movement of the robotized acetabular labrum repair device into a plurality of surrounding soft tissues;
wherein the controlling of the robotized acetabular labrum repair device includes causing the robotized acetabular labrum repair device to avoid the safety zone when repairing the unhealthy acetabular labrum.

9. An acetabular labrum repair system comprising:
an acetabular tracking apparatus to generate acetabular tracking data;
an acetabular labrum repair device; and
a robotized surgery controller to:
detect an unhealthy acetabular labrum based on the acetabular tracking data; and
cause the acetabular labrum repair device to repair the unhealthy acetabular labrum.

10. The system of claim 9, further including a robotized cannula placement device, the robotized surgery controller further to control the robotized cannula placement device to place a cannula in a predetermined location to facilitate the repair of the unhealthy acetabular labrum.

11. The system of claim 10, wherein:
the robotized cannula placement device includes a robotized repair device arm to position the robotized acetabular labrum repair device; and
robotized surgery controller is further to control the robotized device arm to facilitate the repair of the unhealthy acetabular labrum.

12. The system of claim 9, wherein the acetabular tracking apparatus includes an arthroscopic camera to generate the acetabular tracking data.

13. The system of claim 9, wherein:
the acetabular tracking apparatus is attached to a robotized tracking device arm to position the acetabular tracking apparatus; and
the robotized surgery controller is further to control the robotized tracking device arm to improve an image quality of the acetabular tracking data.

14. The system of claim 9, further including a robotized surgery tracking apparatus to generate surgery apparatus tracking data, the robotized surgery controller further to determine a location of the robotized acetabular labrum repair device based on the surgery apparatus tracking data.

15. The system of claim 14, wherein:
the surgery apparatus tracking data includes apparatus image data; and
the robotized surgery controller further to process the apparatus image data to identify and determine the location of the robotized acetabular labrum repair device.

16. The system of claim 9, the robotized surgery controller further to:
generate a safety zone, the safety zone representing a plurality of virtual boundaries that prevent movement of the robotized acetabular labrum repair device into a plurality of surrounding soft tissues; and
cause the robotized acetabular labrum repair device to avoid the safety zone when repairing the unhealthy acetabular labrum.

17. At least one non-transitory machine-readable storage medium, comprising a plurality of instructions that, responsive to being executed with processor circuitry of a computer-controlled robotized surgery controller device, cause the device to:
- receive acetabular tracking data from an acetabular tracking apparatus;
- detect an unhealthy acetabular labrum based on the acetabular tracking data; and
- control a robotized acetabular labrum repair device to repair the unhealthy acetabular labrum.

18. The non-transitory machine-readable storage medium of claim 17, the instructions further causing the device to control a robotized cannula placement device to place a cannula in a predetermined location to facilitate the repair of the unhealthy acetabular labrum, wherein:
- the robotized cannula placement device includes a robotized repair device arm to position the robotized acetabular labrum repair device; and
- the instructions further causing the device to control the robotized device arm to facilitate the repair of the unhealthy acetabular labrum.

19. The non-transitory machine-readable storage medium of claim 17, wherein:
- the acetabular tracking apparatus includes an arthroscopic camera to generate the acetabular tracking data;
- the acetabular tracking apparatus is attached to a robotized tracking device arm to position the acetabular tracking apparatus; and
- the instructions further causing the device to control the robotized tracking device arm to improve an image quality of the acetabular tracking data.

20. The non-transitory machine-readable storage medium of claim 17, the instructions further causing the device to:
- receive surgery apparatus tracking data from a robotized surgery tracking apparatus;
- determine a location of the robotized acetabular labrum repair device based on the surgery apparatus tracking data; and
- process apparatus image data within the surgery apparatus tracking data to identify and determine the location of the robotized acetabular labrum repair device.

* * * * *

UNITED STATES PATENT AND TRADEMARK OFFICE
CERTIFICATE OF CORRECTION

PATENT NO. : 11,672,613 B2
APPLICATION NO. : 17/668138
DATED : June 13, 2023
INVENTOR(S) : Amiot et al.

Page 1 of 1

It is certified that error appears in the above-identified patent and that said Letters Patent is hereby corrected as shown below:

On the Title Page

In Column 2, under item (56) "Other Publications", Line 2, delete "Sep. 19," and insert --Mar. 19,-- therefor Signed and Sealed this
Eighth Day of August, 2023

Katherine Kelly Vidal
*Director of the United States Patent and Trademark Office*